(12) United States Patent
Locke et al.

(10) Patent No.: US 10,849,791 B2
(45) Date of Patent: Dec. 1, 2020

(54) DRAPE HAVING MICROSTRAIN INDUCING PROJECTIONS FOR TREATING A WOUND SITE

(71) Applicant: KCI Licensing, Inc., San Antonio, TX (US)

(72) Inventors: Christopher Brian Locke, Bournemouth (GB); Richard Daniel John Coulthard, Verwood (GB); Timothy Mark Robinson, Shillingstone (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 1148 days.

(21) Appl. No.: 15/234,624

(22) Filed: Aug. 11, 2016

(65) Prior Publication Data

US 2016/0346134 A1 Dec. 1, 2016

Related U.S. Application Data

(63) Continuation of application No. 13/311,893, filed on Dec. 6, 2011, now Pat. No. 9,440,010.

(Continued)

(51) Int. Cl.
*A61F 13/00* (2006.01)
*A61L 15/16* (2006.01)
(Continued)

(52) U.S. Cl.
CPC ........ *A61F 13/00068* (2013.01); *A61F 13/00* (2013.01); *A61F 13/00008* (2013.01); *A61F 13/00017* (2013.01); *A61F 13/00034* (2013.01); *A61F 13/00038* (2013.01); *A61F 13/00042* (2013.01); *A61F 13/00046* (2013.01); *A61L 15/00* (2013.01); *A61L 15/16* (2013.01);
(Continued)

(58) Field of Classification Search
CPC ................ A61F 13/02; A61F 13/00068; A61F 13/0216; A61F 13/0203; A61F 2013/00536; A61F 2013/00174; A61F 13/00; A61M 2205/334; A61M 1/009; A61M 1/0088; A61M 1/0023; A61M 1/0025; A61M 27/00; A61M 1/0092; A61L 15/16
USPC ........... 602/43, 53, 41, 42, 54; 604/319, 313
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion for PCT International Application PCT/US11/063403 dated Jun. 4, 2012.
(Continued)

*Primary Examiner* — Victoria J Hicks

(57) ABSTRACT

Systems and apparatuses for administering reduced pressure treatment to a tissue site include a reduced pressure source, a drape having a plurality of projections for contacting the tissue site, and an adhesive connected to at least a portion of the drape for sealing the drape to a portion of a patient's intact epidermis.

20 Claims, 7 Drawing Sheets

Related U.S. Application Data

(60) Provisional application No. 61/420,678, filed on Dec. 7, 2010.

(51) Int. Cl.
*A61L 15/00* (2006.01)
*A61M 1/34* (2006.01)
*A61M 1/00* (2006.01)
*A61L 31/06* (2006.01)

(52) U.S. Cl.
CPC .............. *A61L 31/06* (2013.01); *A61M 1/00* (2013.01); *A61M 1/0023* (2013.01); *A61M 1/0084* (2013.01); *A61M 1/0088* (2013.01); *A61M 1/0092* (2014.02); *A61M 1/34* (2013.01); *A61F 2013/00536* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0028828 A1 | 2/2005 | Heaton et al. |
| 2007/0179419 A1 | 8/2007 | Simpson |
| 2007/0185463 A1 | 8/2007 | Mulligan |
| 2010/0069858 A1 | 3/2010 | Olson |
| 2010/0160876 A1 | 6/2010 | Robinson et al. |
| 2011/0224631 A1 | 9/2011 | Simmons et al. |
| 2011/0230809 A1 | 9/2011 | Manwaring et al. |
| 2012/0123220 A1 | 5/2012 | Iyer et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |

(56) References Cited

FOREIGN PATENT DOCUMENTS

| | | |
|---|---|---|
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 pages English translation thereof.

Davydov, Yu. A., et al; "Vacuum Therapy in the Treatment of Purulent Lactation Mastitis"; Vestnik Khirurgi, May 14, 1986, pp. 66-70, and 9 pages English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 pages English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

DRAPE HAVING MICROSTRAIN INDUCING PROJECTIONS FOR TREATING A WOUND SITE

CROSS-REFERENCE TO RELATED APPLICATIONS

This application is a continuation of U.S. patent application Ser. No. 13/311,893, filed Dec. 6, 2011, which claims the benefit, under 35 USC § 119(e), of U.S. Provisional Patent Application No. 61/420,678, filed Dec. 7, 2010, which is hereby incorporated by reference.

BACKGROUND OF THE INVENTION

1. Field of the Invention

The present invention relates generally to reduced pressure treatment systems and more particularly to a drape having microstrain inducing projections for treating a wound site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

SUMMARY

The problems presented by existing reduced pressure treatment systems are solved by the systems and methods of the illustrative embodiments described herein. In one illustrative embodiment, an apparatus for treating a wound site on a patient includes a drape for positioning over a wound site. The drape includes a substantially gas impermeable, flexible mat having a first side and a second, wound-facing side that is configured to extend beyond the wound site to contact an intact portion of the patient's epidermis. The drape further includes a plurality of projections extending from at least a portion of the second side of the substantially gas impermeable, flexible mat.

In another illustrative embodiment, an apparatus for treating a wound site on a patient includes a single-layer drape for positioning over the wound site configured to (i) extend beyond the wound site to contact a portion of the patient's intact epidermis for sealing the wound site and (ii) promote granulation at the wound site. The drape includes a substantially gas impermeable, flexible sheet having a first side and a second, wound-facing side. The first side of the flexible sheet is substantially smooth and the second side of the sheet has a plurality of projections for promoting granulation formation.

In yet another illustrative embodiment, an apparatus for treating a wound site on a patient includes a multi-layer drape for positioning over a wound site configured to both seal the wound site and promote granulation at the wound site. The drape includes a first layer and a second layer connected to the first layer forming an inner chamber between the first layer and the second layer. The second layer has a first plurality of sections with a thickness, t1, and a second plurality of sections with a thickness, t2, less than the thickness, t1. The second plurality of sections are configured to form a plurality of projections for promoting granulation at the wound site in the presence of a biasing force.

In an illustrative embodiment, an apparatus for treating a wound site on a patient includes a multi-layer drape for positioning over a wound site. The drape is configured to both seal the wound site and promote granulation at the wound site and includes a first layer and a second layer. The second layer is connected to the first layer forming an inner chamber between the first layer and the second layer. The second layer has a plurality of protrusions extending from a tissue-facing side of the second layer in the presence of a biasing force.

In another illustrative embodiment, a reduced pressure treatment system for administering reduced pressure treatment to a tissue site includes a reduced pressure source and a drape in fluid communication with the reduced pressure source to distribute a reduced pressure to the tissue site. The drape includes a substantially gas impermeable, flexible mat having a first side and a second, tissue-facing side that is configured to extend beyond the wound site to contact an intact portion of the patient's epidermis. The drape further includes a plurality of projections extending from at least a portion of the second side of the substantially gas impermeable, flexible mat.

In yet another illustrative embodiment, a reduced pressure treatment system for administering reduced pressure treatment to a tissue site includes a reduced pressure source and a single-layer drape positioned over the tissue site and coupled to the reduced pressure source to distribute a reduced pressure to the tissue site. The drape is configured to (i) extend beyond the tissue site to contact a portion of the patient's intact epidermis for sealing the tissue site and (ii) promote granulation at the tissue site. The drape includes a substantially gas impermeable, flexible sheet having a first side and a second, tissue-facing side such that the first side is substantially smooth and the second side includes a plurality of projections for promoting granulation formation.

In another illustrative embodiment, a reduced pressure treatment system for administering reduced pressure treatment to a tissue site includes a reduced pressure source, a positive pressure source, and a multi-layer drape fluidly coupled to the reduced pressure source and the positive pressure source. The multi-layer drape is positioned over the tissue site and configured to both seal the tissue site and promote granulation at the tissue site. The drape includes a first layer and a second layer connected to the first layer to form an inner chamber between the first layer and the second layer. The second layer has a first plurality of sections with a thickness, t1, and a second plurality of sections with a thickness, t2, less than the thickness, t1. The second plurality of sections are configured to form a plurality of projections for promoting granulation at the wound site in the presence of a positive pressure.

In yet another illustrative embodiment, a reduced pressure treatment system for administering reduced pressure treatment to a tissue site includes a reduced pressure source, a drape having a plurality of projections for contacting the tissue site, and an adhesive connected to at least a portion of the drape for sealing the drape to a portion of a patient's intact epidermis.

Other objects, features, and advantages of the illustrative embodiments will become apparent with reference to the drawings and detailed description that follow.

DETAILED DESCRIPTION OF ILLUSTRATIVE EMBODIMENTS

Figure 1:
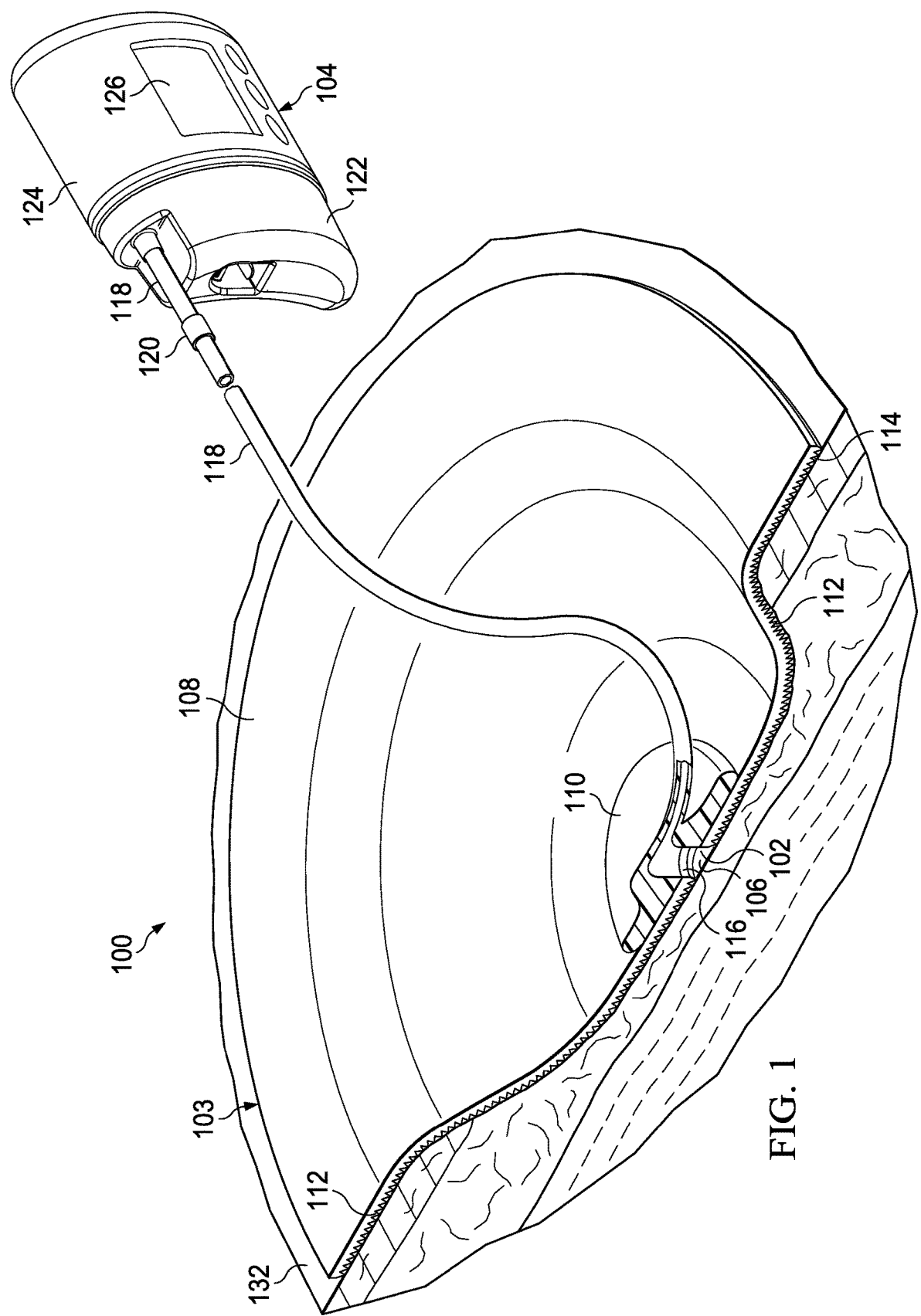
FIG. 1 illustrates a perspective view, with a portion shown in cross-section, of a reduced pressure treatment system including a dressing according to an illustrative embodiment.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "positive pressure" as used herein generally refers to a pressure greater than the ambient pressure at a tissue site that is being subjected to treatment. In some cases, this positive pressure will be greater than the atmospheric pressure at which the patient is located. Alternatively, the positive pressure may be greater than a hydrostatic pressure associated with tissue at the tissue site.

The tissue treatment systems and methods described in this application improve the treatment of a tissue site by increasing or improving granulation tissue development, thus allowing healing of a wound that may not otherwise heal with traditional treatment modalities, or in some cases, allowing an increased rate of healing of a wound. Granulation may be promoted by exposing the tissue site to micro-mechanical stresses and strains. The tissue site may also be exposed to macro strains. While the creation of micro-mechanical stresses and strains at a tissue site may be provided by applying a reduced pressure to a sealed space adjacent the tissue site, the system and methods described herein may also employ the use of positive pressure or forces to create micro and macro stresses and strains.

Referring to FIG. 1, an illustrative embodiment of a reduced pressure treatment system 100 for treating a tissue site 102 on a patient includes a dressing 103 placed proximate to the tissue site 102 and a therapy unit 104 fluidly coupled to the dressing 103. As used herein, the term "tissue site" may refer to a wound, such as a wound 106, or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The dressing 103 includes a drape 108, having a plurality of projections 112 extending from the drape 108 and positioned in contact with the tissue site 102. The plurality of projections 112 are configured to create microstrain at the tissue site 102 when reduced pressure is applied to stimulate the formation of granulation tissue. The drape 108 is positioned over the tissue site 102 to create a sealed space 114 between the drape 108 and the tissue site 102. Thus, the drape 108 is configured to not only create the sealed space 114, but to also stimulate the formation of granulation at the tissue site 102.

The dressing 103 further includes a reduced pressure interface 110 fluidly coupling the drape 108 to the therapy unit 104. The reduced pressure interface 110 is fluidly coupled to the drape 108 to provide fluid access to the tissue site 102. The drape 108 includes an aperture 116 for providing fluid access to the reduced pressure interface 110. A conduit 118 fluidly couples the therapy unit 104 and the reduced pressure interface 110. The reduced pressure interface 110 is capable of delivering reduced pressure to the tissue site 102.

In one embodiment, the therapy unit 104 includes a fluid containment member 122 in fluid communication with a reduced pressure source 124. In the embodiment illustrated in FIG. 1, the fluid containment member 122 is a collection canister that includes a chamber for collecting fluids from the tissue site 102. The fluid containment member 122 alternatively could be an absorbent material or any other container, device, or material that is capable of collecting fluid.

The conduit 118 may be a multi-lumen tube that is capable of providing one or more conduits to deliver reduced pressure to the drape 108 and one or more conduits to sense the amount of pressure at the tissue site 102. Liquids or exudates communicated from the drape 108 through the conduit 118 are removed from the conduit 118 and retained within the fluid containment member 122.

Referring still to FIG. 1, the reduced pressure source 124 may an electrically-driven vacuum pump. In another implementation, the reduced pressure source 124 may instead be a manually-actuated or manually-charged pump that does not require electrical power. In one embodiment, the reduced pressure source 124 may be one or more piezoelectric-actuated micropumps that may be positioned remotely from the dressing 103, or at the dressing beneath or adjacent to the drape 108. The reduced pressure source 124 instead may be any other type of pump, or alternatively a wall suction port or air delivery port such as those available in hospitals and other medical facilities. The reduced pressure source 124 may be housed within or used in conjunction with the therapy unit 104, which may also contain sensors, processing units, alarm indicators, memory, databases, software, display units, and user interfaces 126 that further facilitate the application of reduced pressure treatment to the tissue site 102. In one example, pressure-detection sensors (not shown) may be disposed at or near the reduced pressure source 124. The pressure-detection sensors may receive pressure data from the reduced pressure interface 110 via lumens in the conduit 118 that are dedicated to delivering reduced pressure data to the pressure-detection sensors. The pressure-detection sensors may communicate with a processing unit that monitors and controls the reduced pressure that is delivered by the reduced pressure source 124.

The reduced pressure treatment system 100 may further include a vent 120 in the conduit 118 configured to release the reduced pressure at the tissue site 102 over a selected amount of time. A sensor (not shown) positioned in the therapy unit 104 may receive data from the vent 120. The sensor communicates with the processing unit. The measurements from the sensor may be used by the processing unit to determine a real-time rate of pressure decay as the reduced pressure is released through the vent 120. Based on repeated determinations of the real-time rate of pressure decay, the processing unit is configured to determine whether the drape 108 needs to be replaced due to the growth of granulation tissue or the accumulation of slough, i.e., dead tissue. More rapid rates of pressure decay may indicate that the drape 108 needs to be replaced. The decay of the reduced pressure may be determined in several ways. For example, the decay may be determined by measuring a reduction in the reduced pressure (i.e. increase in absolute pressure) over a selected amount of time after opening the vent 120. As another example, the decay may be determined by measuring the amount of time that is required for the reduced pressure to drop to a threshold pressure. The decay in reduced pressure may also be determined by measuring the reduction in the flow rate in the conduit 118 over the selected amount of time after opening the vent 120. Other methods of measuring the decay of reduced pressure may also be used in a similar manner and are contemplated within the scope of the illustrative embodiments.

The processing unit may send an alert signal to an alarm when the drape 108 needs to be changed. In addition to the processing unit sending an alert signal, the processing unit may further indicate whether the drape 108 needs to be changed due to an accumulation of slough, or whether the drape 108 needs to be changed due to the growth of granulation tissue. The shape of the pressure-time curve would distinguish between slough and granulation tissue. Slough tends to be softer than granulation tissue so when reduced pressure is applied to the drape 108, more time would pass in reaching the set pressure when the drape 108 has been placed adjacent to slough. More time would pass to reach the set pressure due to the compression or creep of the slough as it is squeezed between the drape 108 and the tissue site 102.

Referring now primarily to FIGS. 1-4B, the dressing 103, and in particular the drape 108, will be described in more detail. The drape 108, having a first side 128 and a second, tissue-facing side 130, is positioned over the tissue site 102. The plurality of projections 112 are located on at least a portion of the second side 130 of the drape 108 and are configured to create microstrain at the tissue site 102 to promote granulation. As illustrated, the drape 108 is comprised of a single layer. The drape 108 may be a biomedical grade silicone or another flexible, biomedical material such as polyurethane (PU), and particularly a hydrophilic polyurethane, that may be easily removed from the tissue site 102 even in the presence of granulation formation. The materials used to form the drape 108 may have elastic properties that assist in preventing the tissue site 102 from contracting when the drape 108 is stretched into the tissue site 102 under reduced pressure. In other words, the stretching of the drape 108 into the tissue site 102 creates macrostrain at the tissue site 102 that assists in preventing wound contraction. In one embodiment, the material used to form the drape 108 is substantially transparent to allow a healthcare provider to inspect the tissue site 102 without removing the drape 108. The drape 108 may be formed in a number of ways. In specific, non-limiting examples, the drape 108 may be formed by extrusion or molding.

The drape 108 may further include an adhesive layer (not explicitly shown). A liner may cover the adhesive layer to protect or preserve the adhesive layer prior to positioning the drape 108 at the tissue site 102. The adhesive layer is positioned on the second side 130 of the drape 108. The adhesive layer may contact only a portion of the second side 130 of the drape 108, or the adhesive layer may contact the entire second side 130 of the drape 108. In one embodiment, the adhesive layer also contacts the plurality of projections 112 located on the second side 130 of the drape 108. In another embodiment, the adhesive layer only contacts areas of the second side 130 of the drape 108 where the plurality of projections 112 are absent. The adhesive layer may include silver or a hydrogel. The adhesive layer may be configured so that it dissolves in the presence of wound fluid. In another embodiment, the adhesive layer may be inactive until it is contacted with a catalyst. In operation, an area adjacent to the tissue site 102, such as a intact portion of the patient's epidermis 132, may be treated with a catalyst so that when the adhesive layer from the drape 108 contacts the catalyst, the adhesive layer will adhere the drape 108 to the area treated with a catalyst. In another example, the catalyst may be applied directly to the adhesive layer prior to positioning the drape 108 against the tissue site 102 and the surrounding areas of the tissue site 102. In one specific, non-limiting example, the catalyst is a platinum catalyst and the drape 108 includes a silicone. When the platinum catalyst and the silicone are brought into contact, the silicone polymerizes and crosslinks. In another specific, non-limiting example, the catalyst is a multivalent salt such as calcium chloride or zinc chloride. The drape 108 includes a polymer solution such as a sodium salt of an acrylic acid polymer. When the multivalent salt and the polymer solution are brought in contact, the multivalent salt crosslinks with the polymer.

The plurality of projections 112 may be flexible and may further be formed from a substantially gas impermeable material such as silicone. In one embodiment, the plurality of projections 112 may be formed from a semi-gas permeable material. Additionally, the plurality of projections 112 may be rigid. As stated above, the drape 108 may be made from silicone and since the plurality of projections 112 are part of the drape 108, the plurality of projections 112 may also be foamed of silicone. In one embodiment, the plurality of projections 112 are solid. In another embodiment, the plurality of projections 112 are hollow. The plurality of projections 112 may form a plurality of channels 137 to distribute reduced pressure and allow for fluid flow between the plurality of projections 112. The plurality of projections 112 are dimensioned to provide local load points at the tissue site 102 sufficient to create microstrain at the tissue site 102 for stimulating granulation formation when reduced pressure is applied. The pattern or position of the plurality of projections 112 on the drape 108 may be uniform or non-uniform. The plurality of projections 112 may come in a number of shapes. In specific, non-limiting examples, the plurality of projections 112 may be a spike, conical, pyramid, dome, oblong, cylindrical, or rectangular shape. The shape of each of the plurality of projections 112 may be the same, or the shapes of each of the plurality of projections 112 may be different. In a specific, non-limiting embodiment, the shapes will occupy a volume described by cube volumes where the side of the cube would range between approximately 0.2 millimeters (mm) to 1.5 mm. In one embodiment, the spike shape would have a base length or diameter of about 0.2 mm and a vertical height of between 0.4 mm to 0.8 mm. In another embodiment, the cone shape would have a base diameter of about 0.4 mm and a vertical height of between 0.4 mm to 1.2 mm. In yet another embodiment, the dome shape would be a spherical cap or parabolic shape with a base diameter ranging from about 0.4 mm to 1 mm.

Figure 2A:
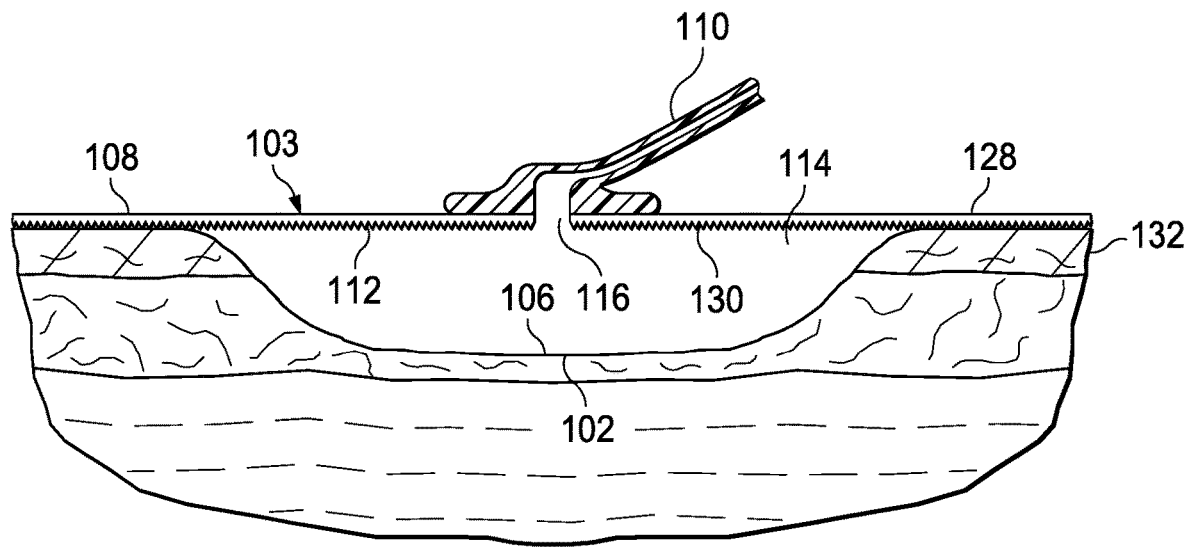
FIG. 2A illustrates a cross-sectional view of an illustrative embodiment of a dressing for use in the reduced pressure treatment system of FIG. 1 without reduced pressure being applied.
Figure 2B:
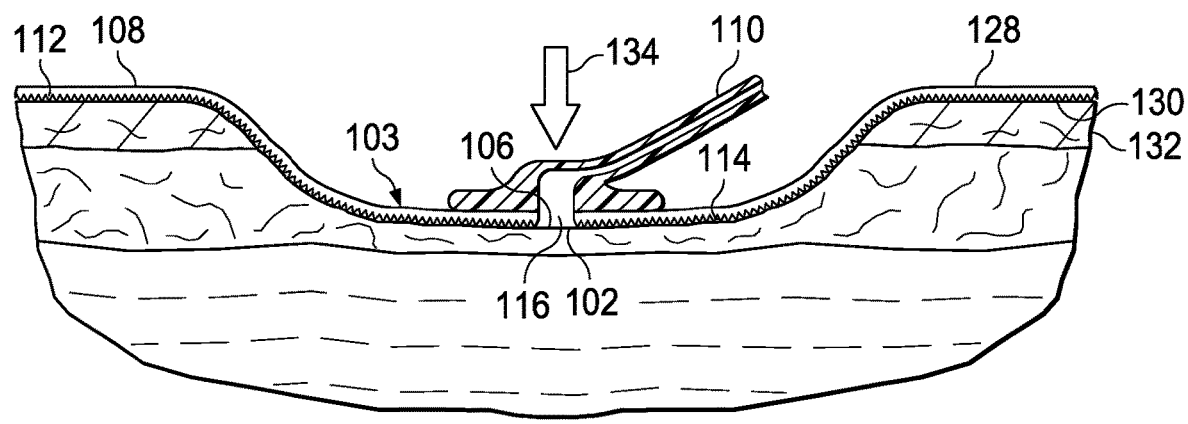
FIG. 2B illustrates a cross-sectional view of an illustrative embodiment of a dressing for use in the reduced pressure treatment system of FIG. 1 with reduced pressure being applied.

Referring now specifically to FIGS. 2A and 2B, the dressing 103 is shown covering the tissue site 102. FIG. 2A illustrates the drape 108 loosely placed over the tissue site 102 prior to the application of reduced pressure. The drape 108 extends beyond the perimeter of the tissue site 102 and contacts the intact portion of the patient's epidermis 132. In this embodiment, FIGS. 2A and 2B show the plurality of projections 112 contacting the intact portion of the patient's epidermis 132. As previously discussed, an adhesive layer seals the drape 108 to the intact portion of the patient's epidermis 132, creating the sealed space 114. FIG. 2B illustrates the drape 108 pressed into the tissue site 102 when reduced pressure has been applied to the sealed space 114. Arrow 134 represents the downward force exerted on the drape 108 when reduced pressure has been applied to the sealed space 114. The reduced pressure applied to the sealed space 114 not only causes the drape 108 to collapse into the tissue site 102 so that the plurality of projections 112 press into the tissue site 102 and create microstrain, the application of reduced pressure also causes the tissue site 102 to be pulled or sucked into the plurality of projections 112. The plurality of channels 137 formed by the plurality of projections 112 allow (1) the reduced pressure to be distributed across the tissue site 102 and (2) fluid to flow around the plurality of projections 112.

Figure 3A:
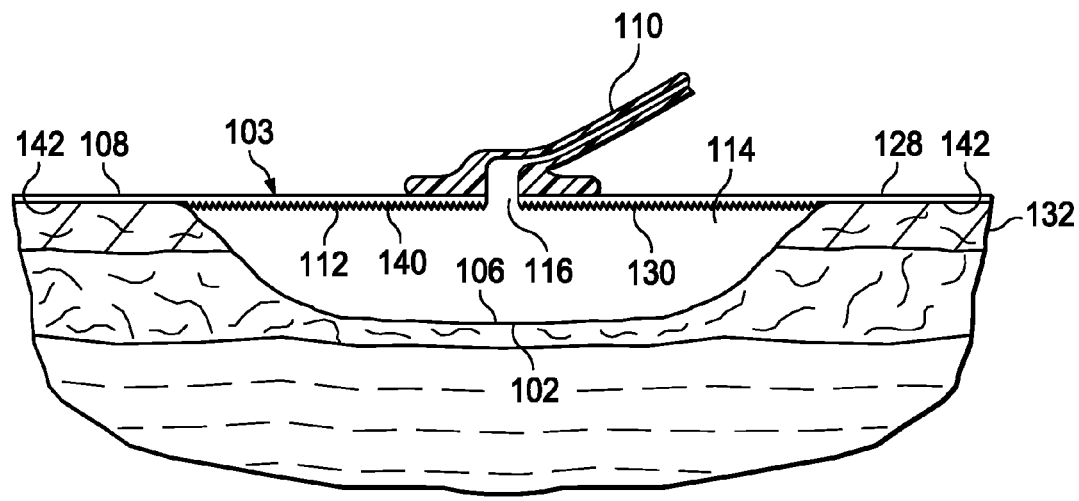
FIG. 3A illustrates a cross-sectional view of an illustrative embodiment of a dressing for use in the reduced pressure treatment system of FIG. 1 without reduced pressure being applied.
Figure 3B:
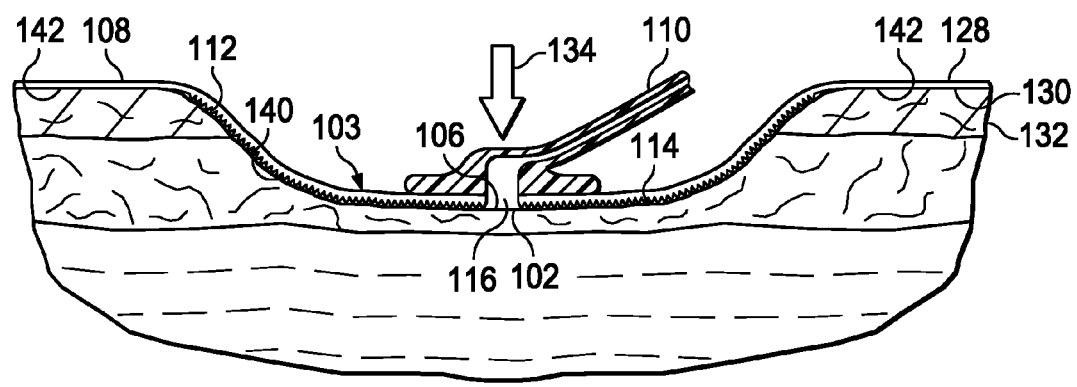
FIG. 3B illustrates a cross-sectional view of an illustrative embodiment of a dressing for use in the reduced pressure treatment system of FIG. 1 with reduced pressure being applied.

Referring now specifically to FIGS. 3A and 3B, the dressing 103 is shown covering the tissue site 102. FIG. 3A illustrates the drape 108 loosely placed over the tissue site 102 prior to the application of reduced pressure. The drape 108 extends beyond the perimeter of the tissue site 102 and contacts the intact portion of the patient's epidermis 132. In this embodiment, FIGS. 3A and 3B show the plurality of projections 112 being limited to an inner portion 140 of the drape 108. Only an outer, smooth portion 142 of the drape 108 contacts the intact portion of the patient's epidermis 132. The outer portion 142 of the drape 108 may surround the inner portion 140 of the drape 108. The adhesive layer seals the drape 108 to the intact portion of the patient's epidermis 132, creating the sealed space 114. FIG. 3B illustrates the drape 108 pressed into the tissue site 102 when reduced pressure has been applied to the sealed space 114. The arrow 134 represents the downward force exerted on the drape 108 when reduced pressure has been applied to the sealed space 114. The reduced pressure applied to the sealed space 114 not only causes the drape 108 to collapse into the tissue site 102 so that the plurality of projections 112 press into the tissue site 102 and create microstrain, the application of reduced pressure also causes the tissue site 102 to be pulled or sucked into the plurality of projections 112. The plurality of channels 137 formed by the plurality of projections 112 allow (1) the reduced pressure to be distributed across the tissue site 102 and (2) fluid to flow around the plurality of projections 112.

Figure 4A:
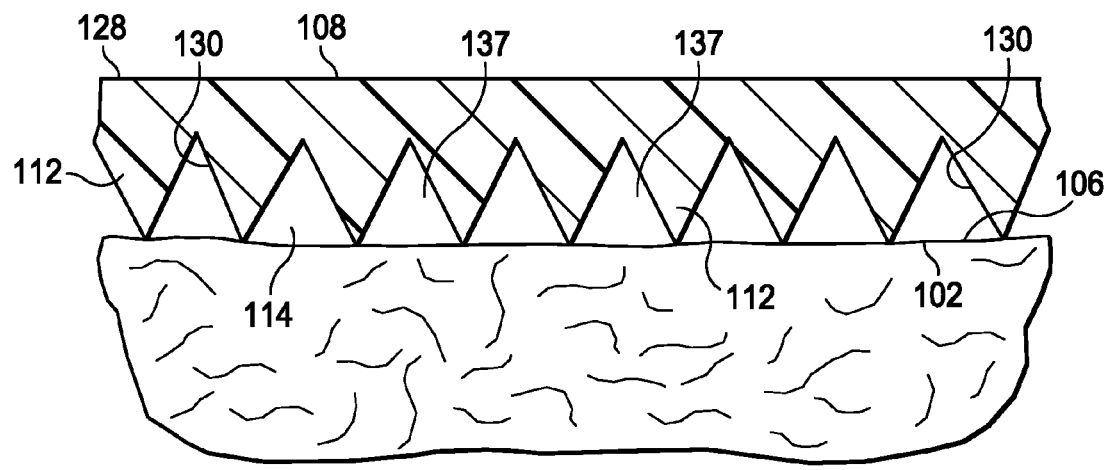
FIG. 4A illustrates a magnified view of a portion of the dressing shown in FIG. 1 without reduced pressure being applied.
Figure 4B:
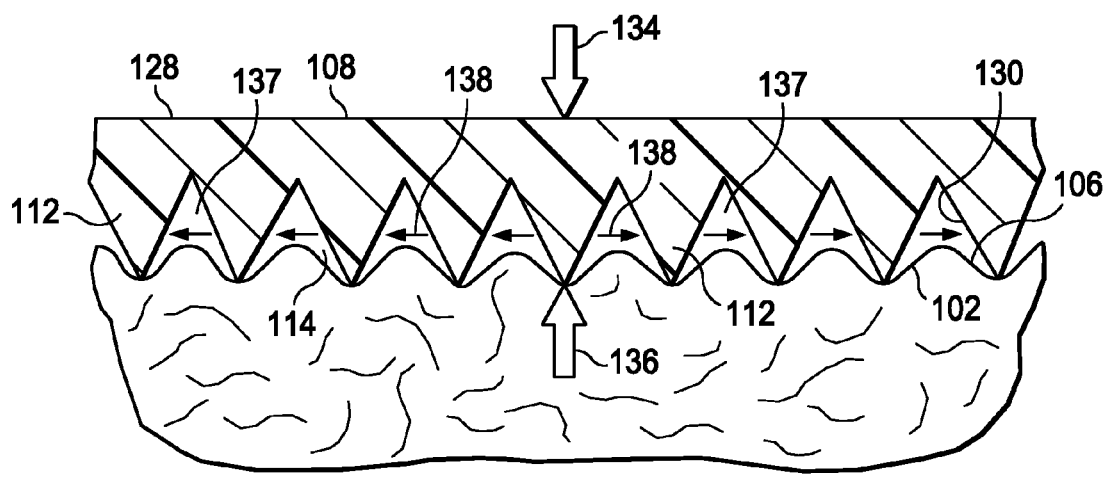
FIG. 4B illustrates a magnified view of a portion of the dressing shown in FIG. 1 with reduced pressure being applied.

Referring now to FIGS. 4A and 4B, a detailed view of a portion the drape 108 is presented. FIG. 4A is a detailed view of the drape 108 positioned over to the tissue site 102 prior to reduced pressure being applied. FIG. 4B is a detailed view of the drape 108 positioned over to the tissue site 102 after reduced pressure has been applied. As shown, the plurality of projections 112 are in the shape of a spike. However, as previously explained, the plurality of projections 112 may take many shapes. The plurality of projections 112 extend from or make up part of the second side 130 of the drape 108. In FIG. 4A the plurality of projections 112 rest against the tissue site 102 without exerting any force on the tissue site 102 caused by reduced pressure. In FIG. 4B, reduced pressure has been applied to the sealed space 114. The arrow 134 represents the force exerted on the drape 108 and, thus, the plurality of projections 112 from the reduced pressure. The arrow 134 represents the force that causes the plurality of projections 112 to be pushed into the tissue site 102. An arrow 136 represents the suction force applied to the tissue site 102 by way of reduced pressure in the sealed space 114. The arrow 136 represents the force that causes the tissue site 102 to pull up against the plurality of projections 112. Arrows 138 may represent the flow of reduced pressure or fluids around the plurality of projections 112 through the plurality of channels 137 formed by the plurality of projections 112.

Figure 5:
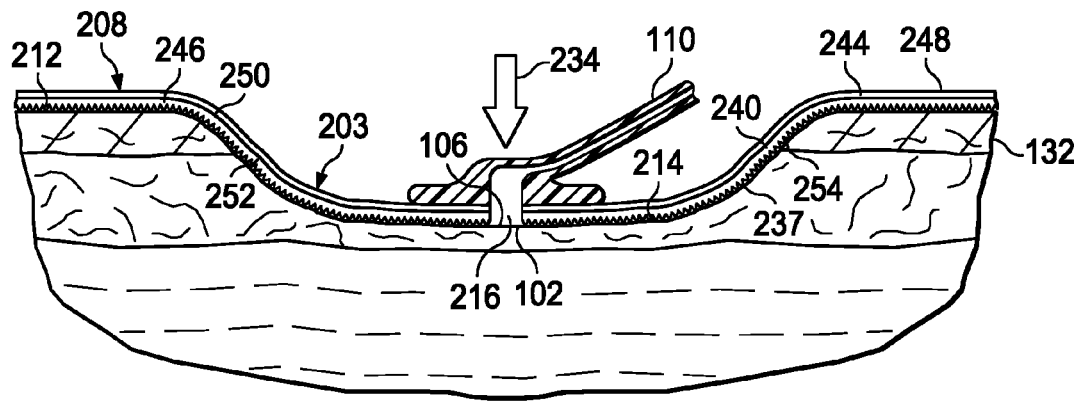
FIG. 5 illustrates a cross-sectional view of an illustrative embodiment of a dressing for use in the reduced pressure treatment system of FIG. 1 with reduced pressure being applied.
Figure 6:
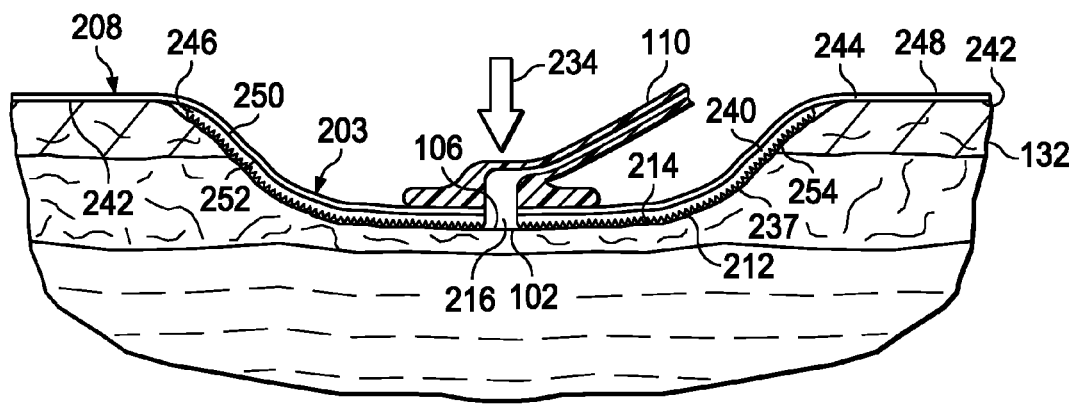
FIG. 6 illustrates a cross-sectional view of an illustrative embodiment of a dressing for use in the reduced pressure treatment system of FIG. 1 with reduced pressure being applied.

Referring now primarily to FIGS. 5 and 6, another embodiment of a drape 208 for use in the reduced pressure treatment system 100 of FIG. 1 is presented. The drape 208 is similar to the drape 108 illustrated in FIGS. 1-4B, except the drape 208 comprises multiple layers. The drape 208 includes a first layer 244 fixed to a second layer 246. The second layer 246 may be referred to as a wound filler. The first layer 244 may be fixed to the second layer 246 by way of bond, weld, adhesive, heat process, or other known connection means. The first layer 244 has a first side 248 and a second side 250. The second layer 246 has a first side 252 and a second side 254. The second side 248 of the first layer 244 is fixed to the first side 252 of the second layer 246. The second side 254 of the second layer 246 includes a plurality of projections 212. The plurality of projections 212 are located on at least a portion of the second side 254 of the second layer 246 of the drape 208. The plurality of projections 212 are configured to create microstrain at the tissue site 102 to promote granulation. In one embodiment (not shown), the second layer may be comprised of only the plurality of projections 212, such that each of the plurality of projections 212 are individually fixed to the first layer 244. The first and second layers 244, 246 of the drape 208 may be formed from a biomedical grade silicone or another flexible, biomedical material such as polyurethane (PLT). In particular the first and second layers 244, 246 may be formed from a hydrophilic polyurethane that may be easily removed from the tissue site 102 even in the presence of granulation formation. The first layer 244 may be formed from the same material or a different material as the second layer 246. The materials used to form the drape 208 may have elastic properties that assist in preventing the tissue site 102 from contracting when the drape 208 is stretched into the tissue site 102 under reduced pressure. In other words, the stretching of the drape 208 into the tissue site 102 creates macrostrain at the tissue site 102 that assists in preventing wound contraction. In one embodiment, the material or materials used to form the drape 208 are substantially transparent to allow a healthcare provider to inspect the tissue site 102 without removing the drape 208. The drape 208 may be formed in a number of ways. In specific, non-limiting examples, the drape 208 may be formed by extrusion or molding.

The drape 208 may further include an adhesive layer (not explicitly shown). A liner may cover the adhesive layer to protect or preserve the adhesive layer prior to positioning the drape 208 at the tissue site 102. The adhesive layer is positioned on the second side 252 of the second layer 246 of the drape 208. The adhesive layer may contact only a portion of the second side 252 of the second layer 246, or the adhesive layer may contact the entire second side 252 of the drape 208. In one embodiment, the adhesive layer also contacts the plurality of projections 212 located on the second side 252 of the second layer 246. In another embodiment, the adhesive layer only contacts areas of the second side 252 of the second layer 246 where the plurality of projections 212 are absent. The adhesive layer may include silver or a hydrogel. The adhesive layer may be configured so that it dissolves in the presence of wound fluid. In another embodiment, the adhesive layer may be inactive until it is contacted with a catalyst. In operation, an area over to the tissue site 102, such as the intact portion of the patient's epidermis 132, may be treated with a catalyst so that when the adhesive layer from the drape 208 contacts the catalyst, the adhesive layer will adhere the drape 208 to the area treated with a catalyst. In another example, the catalyst may be applied directly to the adhesive layer prior to positioning the drape 208 against the tissue site 102 and the surrounding areas of the tissue site 102. In one specific, non-limiting example, the catalyst is a platinum catalyst and the drape 208 includes a silicone. When the platinum catalyst and the silicone are brought into contact, the silicone polymerizes and crosslinks. In another specific, non-limiting example, the catalyst is a multivalent salt such as calcium chloride or zinc chloride. The drape 208 includes a polymer solution such as a sodium salt of an acrylic acid polymer. When the multivalent salt and the polymer solution are brought in contact, the multivalent salt crosslinks with the polymer.

The plurality of projections 212 may be flexible and may further be formed from a substantially gas impermeable material such as silicone. A substantially gas impermeable material may also include a semi-permeable material. In one embodiment, the plurality of projections 212 are rigid. In one embodiment, the plurality of projections 212 are solid. In another embodiment, the plurality of projections 212 are hollow. The plurality of projections 212 form a plurality of channels 237 to distribute reduced pressure and allow for fluid flow between the plurality of projections 212. The plurality of projections 212 are dimensioned to provide local load points at the tissue site 102 sufficient to create microstrain at the tissue site 102 for stimulating granulation formation. The pattern or position of the plurality of projections 212 on the drape 208 may be uniform or non-uniform. The plurality of projections 212 may come in a number of shapes. In specific, non-limiting examples, the plurality of projections 212 may be a spike, conical, pyramid, dome, or oblong shape. The shape of each of the plurality of projections 212 may be the same, or the shapes of each of the plurality of projections 212 may be different.

Referring now specifically to FIG. 5, a dressing 203, which includes the drape 208, is shown covering the tissue site 102. The drape 208 extends beyond the perimeter of the tissue site 102 and contacts the intact portion of the patient's epidermis 132. In this embodiment, FIG. 5 shows the plurality of projections 212 contacting the intact portion of the patient's epidermis 132. As previously discussed, an adhesive layer seals the drape 208 to the intact portion of the patient's epidermis 132, creating a sealed space 214. FIG. 5 illustrates the drape 208 pressed into the tissue site 102 when reduced pressure has been applied to the sealed space 214. Arrow 234 represents the downward force exerted on the drape 208 when reduced pressure has been applied to the sealed space 214. The reduced pressure applied to the sealed space 214 not only causes the drape 208 to collapse into the tissue site 102 so that the plurality of projections 212 press into the tissue site 102 and create microstrain, the application of reduced pressure also causes the tissue site 102 to be pulled or sucked into the plurality of projections 212. The plurality of channels 237 formed by the plurality of projections 212 allow (1) the reduced pressure to be distributed across the tissue site 102 and (2) fluid to flow around the plurality of projections 212.

Referring now specifically to FIG. 6, the dressing 203, which includes the drape 208, is shown covering the tissue site 102. The drape 208 extends beyond the perimeter of the tissue site 102 and contacts the intact portion of the patient's epidermis 132. In this embodiment, FIG. 6 shows the plurality of projections 212 being limited to an inner portion 240 of the drape 208. Only an outer, smooth portion 242 of the drape 208 contacts the intact portion of the patient's epidermis 132. The outer portion 242 of the drape 208 may surround the inner portion 240 of the drape 208. The adhesive layer seals the drape 208 to the intact portion of the patient's epidermis 132, creating the sealed space 214. FIG. 6 illustrates the drape 208 pressed into the tissue site 102 when reduced pressure has been applied to the sealed space 214. The arrow 234 represents the downward force exerted on the drape 208 when reduced pressure has been applied to the sealed space 214. The reduced pressure applied to the sealed space 214 not only causes the drape 208 to collapse into the tissue site 102 so that the plurality of projections 212 press into the tissue site 102 and create microstrain, the application of reduced pressure also causes the tissue site 102 to be pulled or sucked into the plurality of projections 212. The plurality of channels 237 formed by the projections 212 allow (1) the reduced pressure to be distributed across the tissue site 102 and (2) fluid to flow around the plurality of projections 212.

Referring now to FIGS. 7A-8B, another illustrative embodiment of a drape 308 for use in the reduced pressure treatment system 100 of FIG. 1 is presented. The drape 308 is a multi-layer drape for positioning over the tissue site 102 and is configured to (1) provide a sealed space 314 between the drape 308 and the tissue site 102 and (2) promote granulation at the tissue site 102. Similar to the drape 108, the drape 308 may include an adhesive layer for attaching the drape 308 to the tissue site 102 or the intact portion of the patient's epidermis 132 to create the sealed space 314. The reduced pressure interface 110 may be connected to the drape 308 to allow reduced pressure to be applied to the sealed space 314. The drape 308 includes an aperture 316 that allows communication between the reduced pressure interface 110 and the sealed space 314.

The drape 308 includes a first layer 340 and a second layer 342 connected to the first layer 340 that forms an inner space 344 between the first layer 340 and the second layer 342. The second layer 342 is capable of forming a plurality of projections 312 in the presence of a biasing force represented by arrows 346. The plurality of projections 312 are formed in the presence of the biasing force by extending from the second layer 342. In one embodiment, the biasing force is a positive pressure. In this embodiment, the drape 308 includes one or more positive pressure interfaces 348, or pressurization ports. The positive pressure interface 348 is in fluid communication with the inner space 344. The positive pressure interface 348 may be positioned on or attached to the first layer 340. The positive pressure interface 348 allows positive pressure from a positive pressure source (not shown) to be delivered to the inner space 344. In one embodiment, the plurality of projections 312 are formed when a positive pressure, p1, within the inner space 344 is greater than a threshold pressure. In one embodiment, the distance to which the plurality of projections 312 extend from the second layer 342 depends on the level of the positive pressure, p1, within the inner space 344 that is beyond the threshold pressure.

The plurality of projections 312 may be formed by a number of shapes as previously disclosed with reference to the plurality of projections 112. In a specific, non-limiting embodiment, the shape of the plurality of projections 312 when extended from the second layer 342 will occupy a volume described by cube volumes where the side of the cube would range between approximately 0.2 millimeters (mm) to 1.5 mm. In one embodiment, the spike shape would have a base length or diameter of about 0.2 mm and a vertical height of between 0.4 mm to 0.8 mm. In another embodiment, the cone shape would have a base diameter of about 0.4 mm and a vertical height of between 0.4 mm to 1.2 mm. In yet another embodiment, the dome shape would be a spherical cap or parabolic shape with a base diameter ranging from about 0.4 mm to 1 mm.

In one embodiment, the second layer 342 includes a first plurality of sections 350 having a first thickness, t1, and a second plurality of sections 352 having a second thickness, t2. The second thickness, t2, is less than the first thickness, t1. In this embodiment, the second plurality of sections 352 are configured to form the plurality of projections 312 in the presence of the biasing force.

The first layer 340 and the second layer 342 may be formed from the same material. For example, the first layer 340 and the second layer 342 may be formed from silicone or another flexible biomedical material that can be easily removed from the tissue site 102 even in the presence of granulation formation.

Figure 7A:
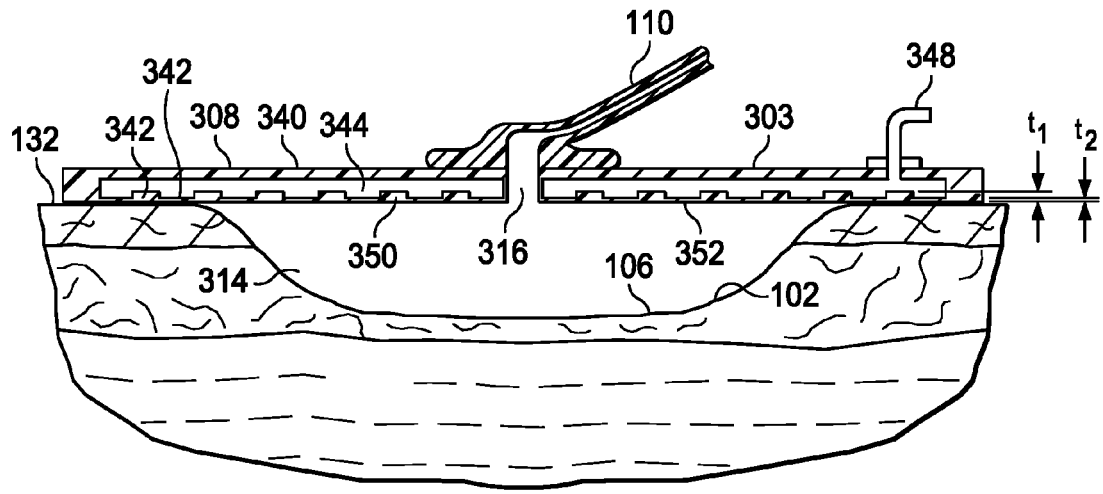
FIG. 7A illustrates a cross-sectional view of an illustrative embodiment of a dressing for use in the reduced pressure treatment system of FIG. 1 without reduced pressure being applied.
Figure 7B:
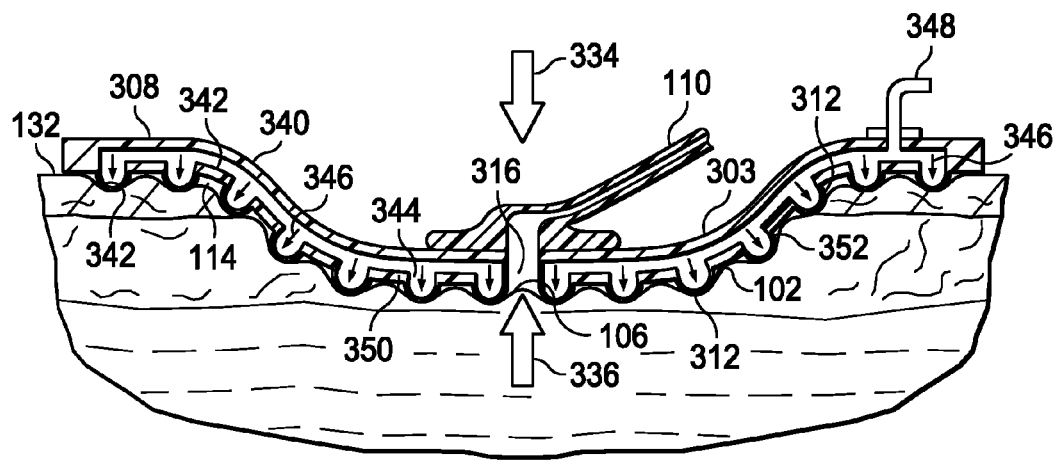
FIG. 7B illustrates a cross-sectional view of an illustrative embodiment of a dressing for use in the reduced pressure treatment system of FIG. 1 with reduced pressure being applied.

Referring now specifically to FIGS. 7A and 7B, a dressing 303 that includes the drape 308 and the reduced pressure interface 110 is shown covering the tissue site 102. FIG. 7A illustrates the drape 308 loosely placed over the tissue site 102 prior to the application of reduced pressure to the sealed space 314 and prior to the application of positive pressure to the inner space 344. The drape 308 extends beyond the perimeter of the tissue site 102 and contacts the intact portion of the patient's epidermis 132. While FIG. 7B shows the plurality of projections 312 contacting the intact portion of the patient's epidermis 132, it should be appreciated that the plurality of projections 312 may be limited to an inner portion of the drape 308 and only an outer, smooth portion of the drape 308 contacts the intact portion of the patient's epidermis 132. The adhesive layer seals the drape 308 to the intact portion of the patient's epidermis 132, creating the sealed space 314. FIG. 7B illustrates the drape 308 after reduced pressure has been applied to the sealed space 314 and after positive pressure has been applied to the inner space 344 at sufficient levels to extend the plurality of projections 312. FIG. 7B shows the plurality of projections 312 pressed against the tissue site 102. Arrow 334 represents the downward force exerted on the drape 308 when reduced pressure has been applied to the sealed space 114. The arrows 346 represent the force exerted on the plurality of projections 312 created by the positive pressure. The reduced pressure applied to the sealed space 314 not only causes the drape 308 to collapse into the tissue site 102 so that the plurality of projections 312 press into the tissue site 102 and create microstrain, the application of reduced pressure also causes the tissue site 102 to be pulled or sucked into the plurality of projections 312.

Figure 8A:
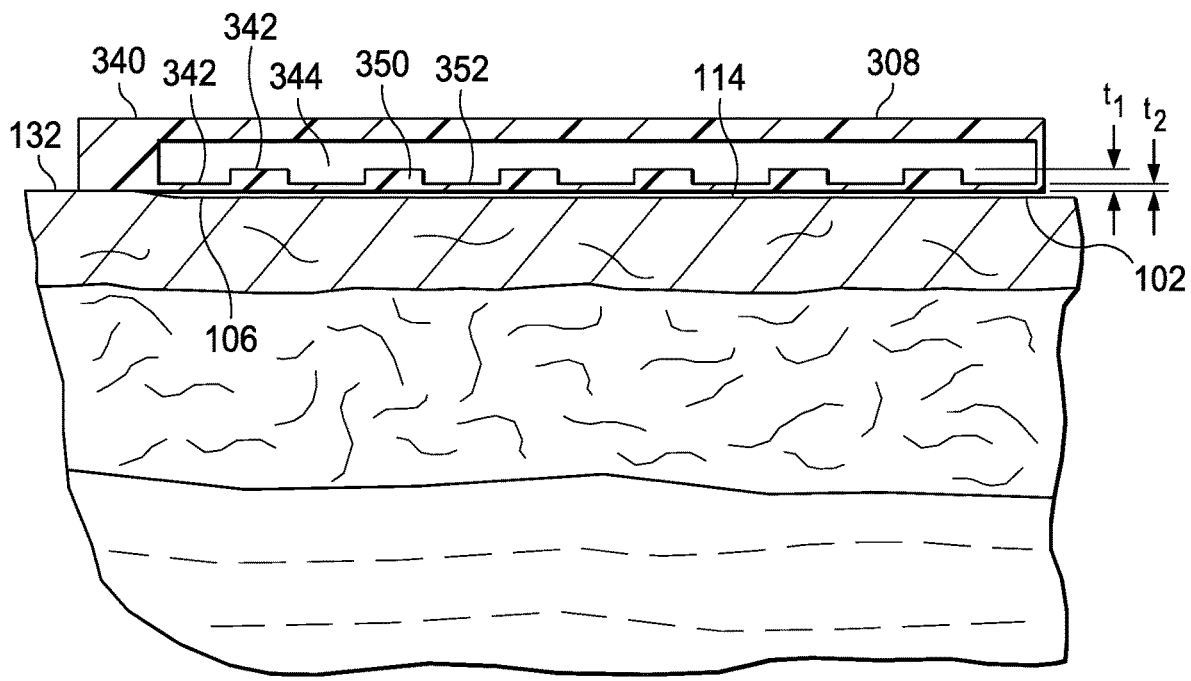
FIG. 8A illustrates a magnified view of a portion of the dressing shown in FIG. 7A.
Figure 8B:
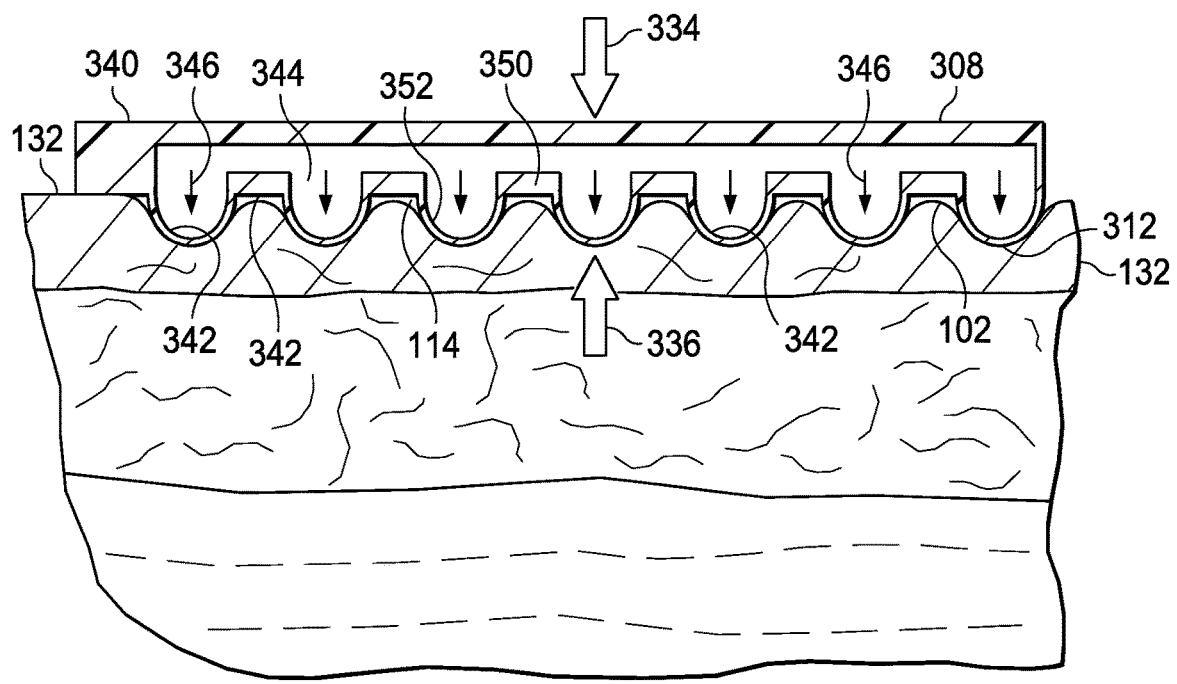
FIG. 8B illustrates a magnified view of a portion of the dressing shown in FIG. 7B.

Referring now to FIGS. 8A and 8B, a detailed view of a portion the drape 308 is presented. FIG. 8A is a detailed view of the drape 308 positioned over to the tissue site 102 prior to reduced pressure being applied. FIG. 8B is a detailed view of the drape 308 positioned over to the tissue site 102 after reduced pressure has been applied to the sealed space 314 and after positive pressure has been applied to the inner space 344 at sufficient levels to form the plurality of projections 312.

It should be apparent from the foregoing that an invention having significant advantages has been provided. While the invention is shown in only a few of its forms, it is not just limited but is susceptible to various changes and modifications without departing from the spirit thereof.

While a number of discrete embodiments have been described, aspects of each embodiment may not be specific to only that embodiment and it is specifically contemplated that features of embodiments may be combined with features of other embodiments.

We claim:

1. An apparatus for treating a tissue site on a patient, the apparatus comprising:
   a drape comprising a substantially gas impermeable, flexible sheet having a tissue-facing side for facing the tissue site, the tissue-facing side including a plurality of projections extending from the tissue-facing side, wherein the drape is configured to be disposed over the tissue site to create a sealed space between the drape and the tissue site with the plurality of projections extending toward the tissue site for promoting tissue formation at the tissue site;
   a reduced pressure interface configured to fluidly couple the sealed space to a source of reduced pressure for providing reduced pressure to the sealed space;
   a vent fluidly coupled to the sealed space to release the reduced pressure from the sealed space after being provided by the source of reduced pressure; and
   a sensor fluidly coupled to the vent for providing data based on a measurement of the reduced pressure being released from the sealed space through the vent and for comparing the data to a predetermined value to provide an alert signal when the data exceeds the predetermined value.

2. The apparatus of claim 1, wherein the data is indicative of tissue formation resulting from application of the reduced pressure to the sealed space and forcing the projections against the tissue site.

3. The apparatus of claim 2, wherein the tissue formation results from growth of granulation tissue to a therapeutic value requiring removal of the drape.

4. The apparatus of claim 2, wherein the tissue formation results from accumulation of dead tissue a therapeutic value requiring removal of the drape.

5. The apparatus of claim 1, wherein the data is determined by measuring a reduction in the reduced pressure over a predetermined period of time.

6. The apparatus of claim 1, wherein the data is determined by measuring an amount of time required for the reduced pressure to drop to a threshold pressure.

7. The apparatus of claim 1, wherein the data is determined by measuring a reduction in flow rate of the reduced pressure over a selected period of time.

8. The apparatus of claim 1, wherein a second side of the drape has a portion configured to extend beyond the tissue site including a surface configured to contact intact epidermis outside the tissue site.

9. The apparatus of claim 8, further comprising an adhesive layer configured to be positioned on at least a portion of the surface of the second side so that the surface is adapted to adhere to the intact epidermis.

10. The apparatus of claim 1, wherein the plurality of projections are dimensioned to provide deformation and microstrain at the tissue site when a reduced pressure has been applied to the tissue site.

11. The apparatus of claim 1, wherein the plurality of projections form a plurality of channels between the plurality of projections when reduced pressure is applied to the sealed space.

12. The apparatus of claim 1, wherein the plurality projections are formed from silicone.

13. The apparatus of claim 1, wherein the drape is sufficiently inelastic to prevent the tissue site from contracting during a healing process.

14. The apparatus of claim 1, wherein the tissue-facing side of the drape has an inner portion and an outer portion surrounding the inner portion, the plurality of projections extend from the inner portion and the outer portion is configured to contact intact epidermis.

15. The apparatus of claim 14, wherein the outer portion is covered with an adhesive layer.

16. The apparatus of claim 1, wherein the sensor comprises:
   a pressure-detection sensor fluidly coupled to the vent and configured to provide the data based on a measurement of the reduced pressure being released from the sealed space through the vent; and
   a processor electrically coupled to the pressure-detection sensor for receiving the data, and configured to compare the data to the predetermined value and provide the alert signal when the data exceeds the predetermined value.

17. An apparatus for treating a tissue site on a patient, the apparatus comprising:
   a drape comprising a substantially gas impermeable, flexible sheet having a tissue-facing side for facing the tissue site, the tissue-facing side including a plurality of projections extending from the tissue-facing side, wherein the drape is configured to be disposed over the tissue site to create a sealed space between the drape and the tissue site with the plurality of projections extending toward the tissue site for promoting tissue formation at the tissue site;
   a reduced pressure interface configured to fluidly couple the sealed space to a source of reduced pressure for providing reduced pressure to the sealed space;
   a vent fluidly coupled to the sealed space to release the reduced pressure from the sealed space after being provided by the source of reduced pressure; and
   a sensor fluidly coupled to the vent and configured to provide data based on a measurement of the reduced pressure being released from the sealed space through the vent and to determine whether the data exceeds a predetermined value for providing an alert signal when the data exceeds the predetermined value.

18. The apparatus of claim 17, wherein the data is determined by measuring a reduction in the reduced pressure over a predetermined period of time.

19. The apparatus of claim 17, wherein the data is determined by measuring an amount of time required for the reduced pressure to drop to a threshold pressure.

20. The apparatus of claim 17, wherein the data is determined by measuring a reduction in flow rate of the reduced pressure over a selected period of time.

* * * * *